(12) United States Patent
Brisken et al.

(10) Patent No.: US 11,944,495 B2
(45) Date of Patent: Apr. 2, 2024

(54) IMPLANTABLE ULTRASONIC VASCULAR SENSOR

(71) Applicant: Foundry Innovation and Research 1, Ltd., Dublin (IE)

(72) Inventors: Axel Brisken, Fremont, CA (US); Jessi Johnson, Sunnyvale, CA (US); Douglas S. Sutton, Pacifica, CA (US); Hanson S. Gifford, III, Woodside, CA (US); Mark Deem, Portola Valley, CA (US); Fiachra Sweeney, Dublin (IE)

(73) Assignee: Foundry Innovation & Research 1, Ltd., Dublin (IE)

( * ) Notice: Subject to any disclaimer, the term of this patent is extended or adjusted under 35 U.S.C. 154(b) by 226 days.

(21) Appl. No.: 16/618,308

(22) PCT Filed: May 31, 2018

(86) PCT No.: PCT/EP2018/064383
§ 371 (c)(1),
(2) Date: Nov. 29, 2019

(87) PCT Pub. No.: WO2018/220143
PCT Pub. Date: Dec. 6, 2018

(65) Prior Publication Data
US 2020/0253583 A1 Aug. 13, 2020

Related U.S. Application Data

(60) Provisional application No. 62/513,013, filed on May 31, 2017.

(51) Int. Cl.
*A61B 8/00* (2006.01)
*A61B 8/08* (2006.01)
*A61B 8/12* (2006.01)

(52) U.S. Cl.
CPC .......... *A61B 8/4472* (2013.01); *A61B 8/0891* (2013.01); *A61B 8/12* (2013.01);
(Continued)

(58) Field of Classification Search
CPC ....... A61B 8/4472; A61B 8/0891; A61B 8/12; A61B 8/4254; A61B 8/5223; A61B 8/565;
(Continued)

(56) References Cited

U.S. PATENT DOCUMENTS 3,568,661 A 3/1971 Franklin
3,838,683 A 10/1974 Kolin
(Continued)

FOREIGN PATENT DOCUMENTS

CN 110613449 B 5/2020
DE 102005035022 A1 11/2006
(Continued)

OTHER PUBLICATIONS

E. Y. Chow et al., "Fully Wireless Implantable Cardiovascular Pressure Monitor Integrated with a Medical Stent," IEEE Transactions on Biomedical Engineering, vol. 57, No. 6, pp. 1487-1496, Jun. 2010 (Year: 2010).*
(Continued)

*Primary Examiner* — Joel Lamprecht
*Assistant Examiner* — Nyrobi Celestine
(74) *Attorney, Agent, or Firm* — Downs Rachlin Martin PLLC (57) ABSTRACT

An implantable ultrasonic vascular sensor for implantation at a fixed location within a vessel, comprising at least one ultrasound transducer, a transducer drive circuit, and means for wirelessly transmitting ultrasound data from the at least one ultrasound transducer.

21 Claims, 4 Drawing Sheets

(52) U.S. Cl.
CPC .......... *A61B 8/4254* (2013.01); *A61B 8/5223* (2013.01); *A61B 8/565* (2013.01)

(58) Field of Classification Search
CPC ......... A61B 5/6862; A61B 8/56; A61B 8/488; A61B 5/6847; A61B 5/0031
See application file for complete search history.

(56) References Cited

U.S. PATENT DOCUMENTS

| | | |
|---|---|---|
| 4,142,412 A | 3/1979 | McLeod |
| 4,638,252 A | 1/1987 | Bradshaw |
| RE32,361 E | 2/1987 | Duggan |
| 4,733,669 A | 3/1988 | Segal |
| 4,926,875 A | 5/1990 | Rabinovitz et al. |
| 4,947,852 A | 8/1990 | Nassi et al. |
| 5,127,404 A | 7/1992 | Wyborny et al. |
| 5,205,292 A | 4/1993 | Czar et al. |
| 5,316,001 A | 5/1994 | Ferek-Petric et al. |
| 5,339,816 A | 8/1994 | Akamatsu et al. |
| 5,363,848 A | 11/1994 | Spani et al. |
| 5,476,484 A | 12/1995 | Hedberg |
| 5,495,852 A | 3/1996 | Stadler et al. |
| 5,630,836 A | 5/1997 | Prem et al. |
| 5,752,522 A | 5/1998 | Murphy |
| 5,872,520 A | 2/1999 | Siefert et al. |
| 5,902,308 A | 5/1999 | Murphy |
| 5,967,986 A | 10/1999 | Cimochowski |
| 5,971,933 A | 10/1999 | Gopakumaran |
| 6,010,511 A | 1/2000 | Murphy |
| 6,012,457 A | 1/2000 | Lesh |
| 6,015,386 A | 1/2000 | Kensey et al. |
| 6,025,725 A | 2/2000 | Gershenfeld et al. |
| 6,039,701 A | 3/2000 | Sliwa et al. |
| 6,053,873 A | 4/2000 | Govari et al. |
| 6,111,520 A | 8/2000 | Allen et al. |
| 6,115,633 A | 9/2000 | Lang et al. |
| 6,115,636 A | 9/2000 | Ryan |
| 6,164,283 A | 12/2000 | Lesh |
| 6,206,835 B1 | 3/2001 | Spillman, Jr. et al. |
| 6,231,516 B1 * | 5/2001 | Keilman .............. A61B 5/0031 600/481 |
| 6,261,233 B1 | 7/2001 | Kantorovich |
| 6,278,379 B1 | 8/2001 | Allen et al. |
| 6,287,253 B1 | 9/2001 | Ortega et al. |
| 6,325,762 B1 | 12/2001 | Tjin |
| 6,339,816 B1 | 1/2002 | Bausch |
| 6,354,999 B1 | 3/2002 | Dgany et al. |
| 6,398,734 B1 | 6/2002 | Cimochowski et al. |
| 6,434,411 B1 | 8/2002 | Duret |
| 6,503,202 B1 | 1/2003 | Hossack et al. |
| 6,574,510 B2 | 6/2003 | Von Arx et al. |
| 6,673,020 B2 | 1/2004 | Okada et al. |
| 6,699,186 B1 | 3/2004 | Wolinsky et al. |
| 6,738,671 B2 | 5/2004 | Christophersom et al. |
| 6,776,763 B2 * | 8/2004 | Nix .......................... A61B 8/12 156/218 |
| 6,802,811 B1 | 10/2004 | Slepian |
| 6,855,115 B2 | 2/2005 | Fonseca |
| 6,895,265 B2 * | 5/2005 | Silver .................. A61B 5/0031 600/345 |
| 6,926,670 B2 | 8/2005 | Rich et al. |
| 6,972,553 B2 | 12/2005 | Petrovich et al. |
| 7,065,409 B2 | 6/2006 | Mazar |
| 7,077,812 B2 | 7/2006 | Naghavi |
| 7,082,330 B2 | 7/2006 | Stadler et al. |
| 7,147,604 B1 | 12/2006 | Allen |
| 7,149,587 B2 | 12/2006 | Wardle et al. |
| 7,191,013 B1 | 3/2007 | Miranda et al. |
| 7,225,032 B2 | 5/2007 | Schmeling et al. |
| 7,233,821 B2 | 6/2007 | Hettrick et al. |
| 7,236,821 B2 | 6/2007 | Cates et al. |
| 7,245,117 B1 | 7/2007 | Joy |
| 7,284,442 B2 | 10/2007 | Fleischman et al. |
| 7,367,984 B2 | 5/2008 | Kulcinski et al. |
| 7,423,496 B2 | 9/2008 | Scheuermann |
| 7,432,723 B2 | 10/2008 | Ellis |
| 7,439,723 B2 | 10/2008 | Allen |
| 7,444,878 B1 | 11/2008 | Pepples |
| 7,452,334 B2 | 11/2008 | Gianchandani et al. |
| 7,454,244 B2 | 11/2008 | Kassab et al. |
| 7,466,120 B2 | 12/2008 | Miller |
| 7,479,112 B2 | 1/2009 | Sweeney et al. |
| 7,481,771 B2 | 1/2009 | Fonseca |
| 7,492,144 B2 | 2/2009 | Powers |
| 7,498,799 B2 | 3/2009 | Allen |
| 7,550,978 B2 | 6/2009 | Joy |
| 7,574,792 B2 | 8/2009 | O'Brien |
| 7,595,647 B2 | 9/2009 | Kroh |
| 7,618,363 B2 | 11/2009 | Yadav |
| 7,621,036 B2 | 11/2009 | Cros |
| 7,621,876 B2 | 11/2009 | Hoctor et al. |
| 7,647,831 B2 | 1/2010 | Corcoran |
| 7,647,836 B2 | 1/2010 | O'Brien |
| 7,662,653 B2 | 2/2010 | O'Brien |
| 7,667,547 B2 | 2/2010 | Ellis |
| 7,677,107 B2 | 3/2010 | Nunez |
| 7,678,135 B2 | 3/2010 | Maahs et al. |
| 7,679,355 B2 | 3/2010 | Allen |
| 7,699,059 B2 | 4/2010 | Fonseca |
| 7,710,103 B2 | 5/2010 | Powers |
| 7,725,160 B2 | 5/2010 | Weber |
| 7,748,277 B2 | 7/2010 | O'Brien |
| 7,778,684 B2 | 8/2010 | Weber et al. |
| 7,786,867 B2 | 8/2010 | Hamel et al. |
| 7,812,416 B2 | 10/2010 | Courcimault |
| 7,829,363 B2 | 11/2010 | You |
| 7,839,153 B2 | 11/2010 | Joy |
| 7,848,813 B2 | 12/2010 | Bergelson et al. |
| 7,854,172 B2 | 12/2010 | O'Brien |
| 7,908,002 B2 | 3/2011 | Hoijer |
| 7,908,018 B2 | 3/2011 | O'Brien |
| 7,909,770 B2 | 3/2011 | Stern |
| 7,932,732 B2 | 4/2011 | Ellis |
| 7,936,174 B2 | 5/2011 | Ellis |
| 7,955,269 B2 | 6/2011 | Stahmann |
| 7,966,886 B2 | 6/2011 | Corcoran |
| 7,988,719 B2 | 8/2011 | Alt et al. |
| 8,016,766 B2 | 9/2011 | Goedje et al. |
| 8,021,307 B2 | 9/2011 | White |
| 8,025,625 B2 | 9/2011 | Allen |
| 8,026,729 B2 | 9/2011 | Kroh |
| 8,060,214 B2 | 11/2011 | Larson et al. |
| 8,078,274 B2 | 12/2011 | Kassab |
| 8,082,032 B2 | 12/2011 | Kassab et al. |
| 8,099,161 B2 | 1/2012 | Kassab |
| 8,107,248 B2 | 1/2012 | Shin et al. |
| 8,111,150 B2 | 2/2012 | Miller |
| 8,114,143 B2 | 2/2012 | Kassab et al. |
| 8,118,749 B2 | 2/2012 | White |
| 8,154,389 B2 | 4/2012 | Rowland |
| 8,159,348 B2 | 4/2012 | Ellis |
| 8,185,194 B2 | 5/2012 | Kassab |
| 8,209,033 B2 | 6/2012 | Zhang et al. |
| 8,221,405 B2 | 7/2012 | Whisenant et al. |
| 8,237,451 B2 | 8/2012 | Joy |
| 8,264,240 B2 | 9/2012 | Park |
| 8,267,954 B2 | 9/2012 | Decant, Jr. et al. |
| 8,278,941 B2 | 10/2012 | Kroh |
| 8,298,147 B2 | 10/2012 | Huennekens et al. |
| 8,298,148 B2 | 10/2012 | Furman |
| 8,353,841 B2 | 1/2013 | White |
| 8,355,777 B2 | 1/2013 | White |
| 8,356,399 B2 | 1/2013 | Kaplan |
| 8,360,984 B2 | 1/2013 | Yadar |
| 8,374,689 B2 | 2/2013 | Gopinathan et al. |
| 8,432,265 B2 | 4/2013 | Rowland |
| 8,442,606 B2 | 5/2013 | Furman |
| 8,442,639 B2 | 5/2013 | Walker et al. |
| 8,465,436 B2 | 6/2013 | Griswold |
| 8,465,452 B2 | 6/2013 | Kassab |
| 8,467,854 B2 | 6/2013 | Lewis et al. |
| 8,493,187 B2 | 7/2013 | Rowland |
| 8,500,660 B2 | 8/2013 | Buchwald et al. |

(56) References Cited

U.S. PATENT DOCUMENTS

| | | |
|---|---|---|
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |
| 8,613,705 B2 | 12/2013 | Scheurer |
| 8,632,469 B2 | 1/2014 | Kassab |
| 8,644,941 B2 | 2/2014 | Rooney et al. |
| 8,665,086 B2 | 3/2014 | Miner |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,706,219 B2 | 4/2014 | Feldman |
| 8,728,012 B2 | 5/2014 | Braido |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,162,065 B2 | 10/2015 | Karst et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,545,263 B2 * | 1/2017 | Lenihan ............ A61B 17/3403 |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,721,463 B2 | 8/2017 | Rowland |
| 9,814,395 B2 | 11/2017 | Stahmann et al. |
| 9,820,673 B2 | 11/2017 | Feldman |
| 9,872,948 B2 | 1/2018 | Siess |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Avi |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 10,335,042 B2 | 7/2019 | Schoenle et al. |
| 10,390,714 B2 | 8/2019 | Wolinsky |
| 10,433,736 B2 | 10/2019 | Karlovsky et al. |
| 10,537,281 B2 | 1/2020 | Thompson et al. |
| 10,542,887 B2 | 1/2020 | Sarkar et al. |
| 10,660,577 B2 | 1/2020 | Thakur et al. |
| 10,548,535 B2 | 2/2020 | Zhang et al. |
| 10,555,704 B2 | 2/2020 | Averina et al. |
| 10,582,866 B2 | 3/2020 | Badie et al. |
| 10,588,528 B2 | 3/2020 | Banet et al. |
| 10,595,734 B2 | 3/2020 | Thakur et al. |
| 10,596,381 B2 | 3/2020 | Averina et al. |
| 10,638,980 B2 | 5/2020 | Gyllensten et al. |
| 10,687,715 B2 | 6/2020 | Jansen et al. |
| 10,702,213 B2 | 7/2020 | Sharma et al. |
| 10,806,352 B2 | 10/2020 | Sweeney et al. |
| 10,905,393 B2 | 2/2021 | Gifford, III et al. |
| 11,006,845 B2 | 5/2021 | Kuraguntla et al. |
| 11,039,813 B2 | 6/2021 | Gifford, III et al. |
| 11,272,840 B2 | 3/2022 | Rothfuss |
| 11,445,924 B2 | 9/2022 | Joseph |
| 11,452,497 B2 | 9/2022 | Garza |
| 2002/0120205 A1 | 8/2002 | Ferek-Petric |
| 2002/0188207 A1* | 12/2002 | Richter ............... A61B 5/6862 600/486 |
| 2003/0037591 A1 | 2/2003 | Ashton et al. |
| 2003/0100940 A1 | 5/2003 | Yodfat |
| 2003/0158584 A1 | 8/2003 | Cates et al. |
| 2003/0199938 A1 | 10/2003 | Smits et al. |
| 2004/0054287 A1* | 3/2004 | Stephens ............ A61B 8/4483 600/459 |
| 2004/0106871 A1 | 6/2004 | Hunyor et al. |
| 2004/0116992 A1 | 6/2004 | Wardle |
| 2004/0133092 A1 | 7/2004 | Kain |
| 2004/0140939 A1 | 7/2004 | Haller et al. |
| 2004/0167596 A1 | 8/2004 | Richter |
| 2004/0176672 A1 | 9/2004 | Silver et al. |
| 2004/0215235 A1 | 10/2004 | Jackson et al. |
| 2004/0225326 A1* | 11/2004 | Weiner ..................... A61F 2/82 607/2 |
| 2005/0137481 A1 | 6/2005 | Sheard et al. |
| 2005/0148903 A1 | 7/2005 | Diamantopoulos |
| 2005/0154321 A1* | 7/2005 | Wolinsky ............ A61B 5/6882 600/483 |
| 2006/0047327 A1 | 3/2006 | Colvin et al. |
| 2006/0056161 A1 | 3/2006 | Shin |
| 2006/0079793 A1 | 4/2006 | Mann et al. |
| 2006/0100522 A1* | 5/2006 | Yuan ..................... H01L 41/183 600/466 |
| 2006/0106321 A1 | 5/2006 | Lewinsky et al. |
| 2006/0122522 A1 | 6/2006 | Chavan et al. |
| 2006/0149166 A1 | 7/2006 | Zvuloni |
| 2006/0174712 A1 | 8/2006 | O'Brien |
| 2006/0177956 A1 | 8/2006 | O'Brien |
| 2006/0178695 A1 | 8/2006 | Decant |
| 2006/0253160 A1 | 11/2006 | Benditt et al. |
| 2006/0271119 A1 | 11/2006 | Ni et al. |
| 2006/0280351 A1 | 12/2006 | Luping et al. |
| 2006/0287602 A1 | 12/2006 | Obrien et al. |
| 2006/0287700 A1 | 12/2006 | White |
| 2007/0088214 A1* | 4/2007 | Shuros ................ A61B 8/4483 600/437 |
| 2007/0129637 A1 | 6/2007 | Wolinsky et al. |
| 2007/0158769 A1 | 7/2007 | You |
| 2007/0199385 A1 | 8/2007 | O'Brien |
| 2007/0249950 A1 | 10/2007 | Piaget et al. |

(56) References Cited

U.S. PATENT DOCUMENTS

| | | |
|---|---|---|
| 2007/0274565 A1 | 11/2007 | Penner |
| 2007/0282210 A1 | 12/2007 | Stern |
| 2007/0292090 A1 | 12/2007 | Alphonse et al. |
| 2008/0015569 A1 | 1/2008 | Saadat |
| 2008/0033527 A1 | 2/2008 | Nunez et al. |
| 2008/0077016 A1 | 3/2008 | Sparks |
| 2008/0097227 A1 | 4/2008 | Zdeblick et al. |
| 2008/0177186 A1 | 7/2008 | Slater et al. |
| 2008/0275350 A1* | 11/2008 | Liao ............... A61B 5/6882 600/486 |
| 2008/0294041 A1 | 11/2008 | Kassab |
| 2009/0007679 A1 | 1/2009 | Nunez |
| 2009/0009332 A1 | 1/2009 | Nunez |
| 2009/0011117 A1 | 1/2009 | Nunez |
| 2009/0024042 A1 | 1/2009 | Nunez |
| 2009/0024177 A1 | 1/2009 | Shuros et al. |
| 2009/0030291 A1 | 1/2009 | O'Brien |
| 2009/0036776 A1 | 2/2009 | Masuda et al. |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1 | 8/2009 | Cauller |
| 2009/0270729 A1 | 10/2009 | Corbucci |
| 2009/0299427 A1 | 12/2009 | Liu et al. |
| 2010/0056922 A1 | 3/2010 | Florent |
| 2010/0063375 A1 | 3/2010 | Kassab et al. |
| 2010/0076398 A1* | 3/2010 | Scheurer ............ A61B 5/0215 600/483 |
| 2010/0094328 A1 | 4/2010 | O'dea et al. |
| 2010/0113939 A1 | 5/2010 | Mashimo et al. |
| 2010/0121398 A1 | 5/2010 | Bjorling et al. |
| 2010/0222786 A1 | 9/2010 | Kassab |
| 2010/0262206 A1 | 10/2010 | Zdeblick et al. |
| 2010/0274217 A1 | 10/2010 | Da Silva et al. |
| 2010/0324432 A1 | 12/2010 | Bjorling et al. |
| 2011/0054333 A1* | 3/2011 | Hoffer ............... A61F 2/91 600/505 |
| 2011/0105863 A1 | 5/2011 | Kroh |
| 2011/0144967 A1 | 6/2011 | Adirovich |
| 2011/0160844 A1 | 6/2011 | Haselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0224582 A1* | 9/2011 | Spence ............ A61M 25/1002 601/2 |
| 2011/0265908 A1 | 11/2011 | Clerc et al. |
| 2011/0306867 A1 | 12/2011 | Gopinathan et al. |
| 2012/0016207 A1 | 1/2012 | Allen |
| 2012/0029598 A1 | 2/2012 | Zhao |
| 2012/0136385 A1 | 5/2012 | Cully |
| 2012/0203090 A1 | 8/2012 | Min |
| 2012/0203113 A1 | 8/2012 | Skerl et al. |
| 2012/0291788 A1 | 11/2012 | Griswold et al. |
| 2012/0296222 A1 | 11/2012 | Griswold et al. |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0060139 A1 | 3/2013 | Richter |
| 2013/0073025 A1 | 3/2013 | Kassab |
| 2013/0085350 A1* | 4/2013 | Schugt ............... A61B 5/0031 607/59 |
| 2013/0096409 A1 | 4/2013 | Hiltner et al. |
| 2013/0178750 A1 | 7/2013 | Sheehan et al. |
| 2013/0178751 A1 | 7/2013 | Min |
| 2013/0184545 A1 | 7/2013 | Blomqvist et al. |
| 2013/0218054 A1 | 8/2013 | Sverdlik et al. |
| 2013/0222153 A1 | 8/2013 | Rowland et al. |
| 2013/0245469 A1 | 9/2013 | Yadav |
| 2013/0245745 A1 | 9/2013 | Vong et al. |
| 2013/0261655 A1 | 10/2013 | Drasler et al. |
| 2013/0274705 A1 | 10/2013 | Burnes et al. |
| 2013/0281800 A1 | 10/2013 | Saroka et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0073935 A1 | 3/2014 | Rodriguez-Llorente |
| 2014/0084943 A1 | 3/2014 | Kroh |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0180118 A1* | 6/2014 | Stigall ............... A61B 8/12 600/463 |
| 2014/0200428 A1 | 7/2014 | Kassab |
| 2014/0236011 A1 | 8/2014 | Fan et al. |
| 2014/0243640 A1 | 8/2014 | O'Dea |
| 2014/0266935 A1 | 9/2014 | Tankiewicz |
| 2014/0275861 A1 | 9/2014 | Kroh |
| 2014/0276011 A1 | 9/2014 | Schmitt et al. |
| 2014/0276067 A1* | 9/2014 | Neasham ............ A61B 8/42 600/446 |
| 2014/0276110 A1 | 9/2014 | Hoseit |
| 2014/0276121 A1 | 9/2014 | Kassab |
| 2014/0276191 A1 | 9/2014 | Kassab |
| 2014/0288085 A1 | 9/2014 | Yadav |
| 2014/0288459 A1 | 9/2014 | Yadav |
| 2014/0306807 A1 | 10/2014 | Rowland |
| 2014/0330143 A1 | 11/2014 | Kroh et al. |
| 2014/0350348 A1 | 11/2014 | Tee et al. |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bomzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0290373 A1 | 10/2015 | Rudser et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1 | 10/2015 | Kassab |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Lading et al. |
| 2016/0000403 A1 | 1/2016 | Vilkomerson |
| 2016/0015507 A1 | 1/2016 | Johnson et al. |
| 2016/0022216 A1 | 1/2016 | Goldshtein et al. |
| 2016/0022447 A1 | 1/2016 | Kim et al. |
| 2016/0029956 A1 | 2/2016 | Rowland |
| 2016/0029995 A1 | 2/2016 | Navratil et al. |
| 2016/0038087 A1* | 2/2016 | Hunter ............... A61B 5/6862 600/301 |
| 2016/0045184 A1* | 2/2016 | Courtney ............ A61B 8/483 600/424 |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0135941 A1 | 5/2016 | Binmoeller et al. |
| 2016/0166232 A1 | 6/2016 | Merritt |
| 2016/0198981 A1 | 7/2016 | Demir et al. |

(56) References Cited

U.S. PATENT DOCUMENTS

| | | |
|---|---|---|
| 2016/0210846 A1 | 7/2016 | Rowland et al. |
| 2016/0324443 A1 | 11/2016 | Rowland et al. |
| 2016/0345930 A1 | 12/2016 | Mizukami |
| 2017/0055048 A1 | 2/2017 | Nagy et al. |
| 2017/0055909 A1 | 3/2017 | Schibli et al. |
| 2017/0065186 A1* | 3/2017 | Joseph .............. A61B 5/6876 |
| 2017/0071501 A1 | 3/2017 | Kassab |
| 2017/0127975 A1 | 5/2017 | Bozkurt |
| 2017/0164840 A1 | 6/2017 | Matsumoto |
| 2017/0181677 A1 | 6/2017 | Varsavsky et al. |
| 2017/0065824 A1 | 8/2017 | Dagan et al. |
| 2017/0216508 A1 | 8/2017 | Zilbershlag et al. |
| 2017/0224279 A1* | 8/2017 | Cahan .............. A61B 7/045 |
| 2017/0238817 A1 | 8/2017 | Lading |
| 2017/0290686 A1 | 10/2017 | Sirhan et al. |
| 2017/0319096 A1* | 11/2017 | Kaiser .............. A61B 5/445 |
| 2017/0332945 A1 | 11/2017 | Gopinathan et al. |
| 2017/0340440 A1 | 11/2017 | Ratz |
| 2017/0360312 A1 | 12/2017 | Joseph |
| 2018/0014829 A1 | 1/2018 | Tal et al. |
| 2018/0064931 A1 | 3/2018 | Clements |
| 2018/0092631 A1 | 4/2018 | Liou |
| 2018/0172785 A1 | 6/2018 | Leussler et al. |
| 2018/0177486 A1 | 6/2018 | Gifford et al. |
| 2018/0220992 A1 | 8/2018 | Gifford et al. |
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0271371 A1 | 9/2018 | Ziaie et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2018/0326151 A1 | 11/2018 | Halpert et al. |
| 2018/0344917 A1 | 12/2018 | Inhaber et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Yamada |
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney et al. |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0126014 A1 | 5/2019 | Kapur et al. |
| 2019/0150884 A1 | 5/2019 | Maharbiz et al. |
| 2019/0167188 A1 | 6/2019 | Gifford et al. |
| 2020/0000364 A1 | 1/2020 | Doodeman et al. |
| 2020/0013510 A1 | 1/2020 | Despenic et al. |
| 2020/0022588 A1 | 1/2020 | Wariar et al. |
| 2020/0022589 A1 | 1/2020 | Banet et al. |
| 2020/0029829 A1 | 1/2020 | Banet et al. |
| 2020/0029857 A1 | 1/2020 | Rowland et al. |
| 2020/0030612 A1 | 1/2020 | Song et al. |
| 2020/0037888 A1 | 2/2020 | Thakur et al. |
| 2020/0037892 A1 | 2/2020 | Banet et al. |
| 2020/0046299 A1 | 2/2020 | An et al. |
| 2020/0069857 A1 | 3/2020 | Schwammenthal et al. |
| 2020/0121187 A1 | 4/2020 | Sarkar et al. |
| 2020/0129087 A1 | 4/2020 | Sweeney et al. |
| 2020/0146577 A1 | 5/2020 | Badie et al. |
| 2020/0170515 A1 | 6/2020 | Wen et al. |
| 2020/0170711 A1 | 6/2020 | Hendriks et al. |
| 2020/0187864 A1 | 6/2020 | Sharma |
| 2020/0187865 A1 | 6/2020 | Sharma et al. |
| 2020/0196876 A1 | 6/2020 | Minor et al. |
| 2020/0196899 A1 | 6/2020 | Higgins et al. |
| 2020/0196943 A1 | 6/2020 | Minor et al. |
| 2020/0196944 A1 | 6/2020 | Minor et al. |
| 2020/0196948 A1 | 6/2020 | Cho et al. |
| 2020/0197178 A1 | 6/2020 | Vecchio |
| 2020/0254161 A1 | 8/2020 | Schwammenthal et al. |
| 2020/0289257 A1* | 9/2020 | Marquez .............. A61B 5/4851 |
| 2021/0038094 A1 | 2/2021 | Sweeney et al. |
| 2021/0060298 A1 | 3/2021 | Arndt et al. |
| 2021/0177277 A1 | 6/2021 | Cros et al. |
| 2021/0216733 A1 | 7/2021 | Chronos et al. |
| 2021/0244381 A1 | 8/2021 | Sweeney et al. |
| 2022/0071488 A1 | 3/2022 | Andersen et al. |
| 2022/0125312 A1 | 4/2022 | Nazari et al. |
| 2022/0233084 A1 | 7/2022 | Valdez |
| 2022/0240792 A1 | 8/2022 | Wetterling |
| 2022/0265157 A1 | 8/2022 | Charthad |

FOREIGN PATENT DOCUMENTS

| | | |
|---|---|---|
| EP | 0399059 A1 | 5/1989 |
| EP | 0538885 A1 | 4/1993 |
| EP | 0897285 A1 | 2/1999 |
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 2986252 B1 | 7/2018 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |

(56) References Cited

FOREIGN PATENT DOCUMENTS

| | | |
|---|---|---|
| EP | 3591663 A1 | 1/2020 |
| EP | 3609392 A1 | 2/2020 |
| EP | 3256043 B1 | 3/2020 |
| EP | 3629921 A1 | 4/2020 |
| EP | 3629937 A1 | 4/2020 |
| EP | 3630275 A1 | 4/2020 |
| EP | 3634206 A1 | 4/2020 |
| EP | 3654835 A1 | 5/2020 |
| EP | 3496808 B1 | 6/2020 |
| EP | 2654560 B1 | 7/2020 |
| EP | 3326524 B1 | 7/2020 |
| EP | 3367884 B1 | 7/2020 |
| EP | 3678539 A1 | 7/2020 |
| EP | 3681389 A1 | 7/2020 |
| EP | 3684260 A1 | 7/2020 |
| EP | 3684464 A1 | 7/2020 |
| EP | 2155307 B1 | 3/2021 |
| EP | 4039173 A1 | 8/2022 |
| GB | 2473529 A | 3/2011 |
| JP | 2011234884 A | 11/2011 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004014456 A2 | 2/2004 |
| WO | 2004073796 A1 | 9/2004 |
| WO | 2006049796 A2 | 5/2006 |
| WO | 2006086113 A2 | 8/2006 |
| WO | 2006086114 A2 | 8/2006 |
| WO | 2005027998 A2 | 9/2006 |
| WO | 2006094273 A2 | 9/2006 |
| WO | 2006096582 A1 | 9/2006 |
| WO | 2006102905 A1 | 10/2006 |
| WO | 2006110798 A2 | 10/2006 |
| WO | 2006025215 A2 | 11/2006 |
| WO | 2007002185 A2 | 1/2007 |
| WO | 2007002224 A2 | 1/2007 |
| WO | 2007002225 A2 | 1/2007 |
| WO | 2007008493 A1 | 1/2007 |
| WO | 2007028035 A2 | 3/2007 |
| WO | 2007035332 A1 | 3/2007 |
| WO | 2007047571 A2 | 4/2007 |
| WO | 2007047794 A2 | 4/2007 |
| WO | 2007061841 A2 | 5/2007 |
| WO | 2007106490 A2 | 9/2007 |
| WO | 2007106533 A1 | 9/2007 |
| WO | 2007130628 A2 | 11/2007 |
| WO | 2008031011 A1 | 3/2008 |
| WO | 2008031095 A1 | 3/2008 |
| WO | 2008051907 A1 | 5/2008 |
| WO | 2008066569 A2 | 6/2008 |
| WO | 2009006602 A1 | 1/2009 |
| WO | 2009006608 A1 | 1/2009 |
| WO | 2009006610 A1 | 1/2009 |
| WO | 2009006615 A1 | 1/2009 |
| WO | 2009025648 A1 | 2/2009 |
| WO | 2009039174 A1 | 3/2009 |
| WO | 2009111255 A1 | 9/2009 |
| WO | 2009131879 A1 | 10/2009 |
| WO | 2011060359 A2 | 11/2009 |
| WO | 2009146089 A2 | 12/2009 |
| WO | 2009146090 A1 | 12/2009 |
| WO | 2009149462 A2 | 12/2009 |
| WO | 2010011612 A1 | 1/2010 |
| WO | 2010088279 A2 | 8/2010 |
| WO | 2010117597 A1 | 10/2010 |
| WO | 20100117356 A1 | 10/2010 |
| WO | 2011011104 A1 | 1/2011 |
| WO | 2012015954 A1 | 2/2012 |
| WO | 2012015955 A1 | 2/2012 |
| WO | 2012019191 A2 | 2/2012 |
| WO | 2012090206 A2 | 7/2012 |
| WO | 2012140147 A3 | 10/2012 |
| WO | 2012145187 A1 | 10/2012 |
| WO | 2012149008 A2 | 11/2012 |
| WO | 2013003754 A1 | 1/2013 |
| WO | 2013142387 A1 | 9/2013 |
| WO | 2013163605 A1 | 10/2013 |
| WO | 2014006471 A2 | 1/2014 |
| WO | 2014012670 A1 | 1/2014 |
| WO | 2004014456 A2 | 2/2014 |
| WO | 2014047528 A1 | 3/2014 |
| WO | 2014054045 A1 | 4/2014 |
| WO | 2014070316 A1 | 5/2014 |
| WO | 2014076620 A2 | 5/2014 |
| WO | 2014081958 A1 | 5/2014 |
| WO | 2014145531 A1 | 9/2014 |
| WO | 2014145712 A1 | 9/2014 |
| WO | 2014162181 A2 | 10/2014 |
| WO | 2014170771 A1 | 10/2014 |
| WO | 2014179739 A1 | 11/2014 |
| WO | WO-2014188430 A2 * | 11/2014 ............... A61N 7/00 |
| WO | 2014197101 A1 | 12/2014 |
| WO | 2015074018 A1 | 5/2015 |
| WO | 2015109028 A1 | 7/2015 |
| WO | 20150157712 A2 | 10/2015 |
| WO | 2016011309 A2 | 1/2016 |
| WO | 2016025430 A1 | 2/2016 |
| WO | 2016131020 A1 | 8/2016 |
| WO | 2016156446 A1 | 10/2016 |
| WO | 2016178196 A2 | 11/2016 |
| WO | 2016178197 A1 | 11/2016 |
| WO | 2017024051 A1 | 2/2017 |
| WO | 2017143198 A1 | 8/2017 |
| WO | 2017198867 A1 | 11/2017 |
| WO | 2017222964 A1 | 12/2017 |
| WO | 2018013725 A1 | 1/2018 |
| WO | 2018031714 A1 | 2/2018 |
| WO | 2018081314 A1 | 5/2018 |
| WO | 2018102435 A1 | 6/2018 |
| WO | 2018146690 A1 | 8/2018 |
| WO | 2018150314 A1 | 8/2018 |
| WO | 2018156930 A1 | 8/2018 |
| WO | 2018187582 A1 | 10/2018 |
| WO | 2018220143 A1 | 12/2018 |
| WO | 2018220146 A1 | 12/2018 |
| WO | 2019050831 A1 | 3/2019 |
| WO | 2019051007 A1 | 3/2019 |
| WO | 2019051108 A1 | 3/2019 |
| WO | 2019051007 A8 | 4/2019 |
| WO | 2019063521 A1 | 4/2019 |
| WO | 2019079364 A1 | 4/2019 |
| WO | 2019232213 A1 | 12/2019 |
| WO | 2020023839 A1 | 1/2020 |
| WO | 2020121221 A1 | 6/2020 |
| WO | 2020131247 A1 | 6/2020 |
| WO | 2020132460 A1 | 6/2020 |
| WO | 2020132668 A2 | 6/2020 |
| WO | 2020132669 A1 | 6/2020 |
| WO | 2020132670 A1 | 6/2020 |
| WO | 2020132671 A1 | 6/2020 |
| WO | 2020132678 A1 | 6/2020 |
| WO | 2020144075 A1 | 7/2020 |
| WO | 2020153765 A2 | 7/2020 |
| WO | 2021217055 A1 | 10/2021 |
| WO | 2021236756 A1 | 11/2021 |
| WO | 2022055920 A1 | 3/2022 |
| WO | 2022167382 A1 | 8/2022 |

OTHER PUBLICATIONS

International Search Report and Written Opinion dated Feb. 27, 2020, in connection with PCT/IB2019/060669 filed Dec. 11, 2019.
Voroneanu et. al., "The relationship between chronic volume overload 3 and elevated blood pressure in hemodialysis patients: 4 use (56) References Cited

OTHER PUBLICATIONS of bioimpedance provides a different perspective 5 from echocardiography and biomarker methodologies," Int Urol Nephrol, Sep. 2010; 42(3):789-97.
Cannesson et al., "Respiratory Variations in Pulse Oximetry Plethysmographic Waveform Amplitude to Predict Fluid Responsiveness in the Operating Room," Anesthesiology 2007; 106:1105-11.
Abraham et al., "The Role of Implantable Hemodynamic Monitors to Manage Heart Failure," Heart Failure Clin 11 (2015) 183-189.
Tallaj et al., "Implantable Hemodynamic Monitors," Cardiol Clin 29 (2011) 289-299.
Tang et al., "Measuring impedance in congestive heart failure: Current options and clinical applications," American Heart Journal 157 (3) 402-411.
Merchant et al., "Implantable Sensors for Heart Failure," Circulation: Arrhythmia and Electrophysiology. 2010; 3:657-667.
Unadkat, Jignesh V., et al. "The Development of a Wireless Implantable Blood Flow Monitor," Ideas and Innovations, American Society of Plastic Surgeons, 136:199 (2015).
Steinhouse, David et al., "Implant Experience with an Implantable Hemodynamic Monitor for the Management of Symptomatic Heart Failure," PACE (Aug. 2005) vol. 28, pp. 747-753.
Braunschweig, Frieder et al. "Dynamic changes in right ventricular pressures during haemodialysis recorded with an implantable haemodynamic monitor," Nephrol Dial Transplant (2006) 21:176-183.
Karamanoglu, Mustafa et al., "Estimation of cardiac output in patients with congestive heart failure by analysis of right ventricular pressure waveforms," BioMedical Engineering OnLine 2011, 10:36.
Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.
Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.
Kjellstrom, Barbo et al., "Changes in Right Ventricular Pressures Between Hemodialysis Sessions Recorded by an Implantable Hemodynamic Monitor," The American Journal of Cardiology, 2009, 103:119-123.
Zile, Michael R. et al., "Transition From Chronic Compensated to Acute Decompensated Heart Failure," Circulation, American Heart Association (2008) 118:1433-1441.
Plicchi, G. et al., "Pea I and Pea II Based Implantable Haemodynamic Monitor: Pre Clinical Studies in Sheep," Europace (2002) 4, 49-54.
Vanderheyden, Marc et al., "Continuous Monitoring of Intrathoracic Impedance and Right Ventricular Pressures in Patients With Heart Failure," Circulation Heart Failure (2010) 3:370-377.
Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.
Muller, Laurent et al., "Respiratory variations of inferior vena cava diameter to predict fluid responsiveness in spontaneously breathing patients with acute circulatory failure: need for a cautious use," Critical Care 2012, 16:R188.
Blehar, David J. et al., "Identification of congestive heart failure via respiratory variation of inferior vena cava diameter." American Journal of Emergency Medicine (2009) 27, 71-75.
Miller, Joseph B., et al., "Inferior vena cava assessment in the bedside diagnosis of acute heart failure," American Journal of Emergency Medicine (2012) 30, 778-783.
Corl, Keith et al., "Bedside sonographic measurement of the inferior vena cava caval index is a poor predictor of fluid responsiveness in emergency department patients," Emergency Medicine Australasia (2012) 24, 534-539.
Feissel, et al. "The respiratory variation in inferior vena cava diameter as a guide to fluid therapy," Intensive Care Med (2004) 30: 1834-1837.
Nakao, Shoichiro et al., "Effects of Positional Changes on Inferior Vena Caval Size and Dynamics and Correlations with Right-Sided Cardiac Pressure," American Journal of Cardiology (1987; 59:125-132).
Saha, Narayan M., et al., "Outpatient Use of Focused Cardiac Ultrasound to Assess the Inferior Vena Cava in Patients With Heart Failure," American Journal of Cardiology (2015).
Ishizaki, et al. "Measurement of inferior vena cava diameter for evaluation of venous return in subjects on day 10 of a bed-rest experiment," J Appl Physical 96: 2179-2186, 2004.
Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & Biol, Eng. & Comput, 1989, 27, 357-364.
Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke Volume in Cardiac Tamponade", Circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).
D. H. Bergel, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T. et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
Extended European Search Report dated Jul. 3, 2020, in connection with EP20163433.4.

(56) References Cited

OTHER PUBLICATIONS

International Search Report and Written Opinion dated Mar. 3, 2020, in connection with PCT/US2019/066589 filed Dec. 16, 2019.
International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
International Search Report and Written Opinion dated Nov. 4, 2019, in connection with PCT/US2019/034657, filed May 30, 2019.
International Search Report and Written Opinion dated Oct. 19, 2017, in connection with PCT/US2017/046204.
Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.
International Search Report and Written Opinion dated Oct. 20, 2016, in connection with PCT/US2016/045385 filed Aug. 3, 2016.
Horizon Scanning Research & Intelligence Centre; Furosemide sc2Wear micro-pump patch for oedema in heart failure; National Institute for Health Research; NIHR HSRIC ID: 11808; Mar. 2016; pp. 1-10; www.hsric.nihr.ac.uk.

\* cited by examiner

P=pulser, L=Limiter, P=Pre-Amplifier, F=Band Pass filter, LA=Linear Amplifier
TGC=Time Gain compensation, C=Compression amplifier

IMPLANTABLE ULTRASONIC VASCULAR SENSOR

RELATED APPLICATIONS

WO2016/131020 and WO2017024051 are filed by the present Assignee and are incorporated by reference herein in their entirety.

FIELD OF THE DISCLOSURE

The present disclosure generally relates to the field of medical devices and methods for monitoring patient blood vessels (or "vascular lumen"), such as the inferior vena cava ("IVC").

INTRODUCTION

Conditions which May be Monitored by IVC or Other Blood Vessel Monitoring

Heart failure is one of the most significant chronic conditions afflicting adult populations. In the United States, 5.7 million Americans have heart failure, with 870,000 new cases annually. As the population ages, this number is growing, as approximately 10% of the population over 80 suffers from heart failure.

In patients with chronic heart failure, significant costs are due to hospitalization to manage acutely decompensated heart failure (ADHF). Each re-hospitalization can last up to a week. ADHF is very often a result of some combination of a downturn in the heart's performance, a downturn in the kidney's removal of fluid from the bloodstream, and/or excessive intake of fluids and/or salt. This leads to a buildup of fluid in the vascular system, resulting in increased blood volume in the left atrium at higher pressure. This eventually leads to fluid filling the lungs and an inability to breathe. Managing these patients to prevent the need for re-hospitalization is extremely challenging. Non-invasive approaches to monitoring patients have been tried, such as weighing patients daily to detect fluid weight gain, or having a nurse call them daily to assess their health status, but these approaches have only modest effectiveness.

Although measurement of left atrial pressure, typically by measuring pulmonary artery wedge pressure, is commonly considered the most direct way to measure congestion in heart failure, there are other areas where congestion can be detected. When additional blood volume is added to the circulatory system, the IVC is one of the first places for that added volume to have an effect. The diameter of the IVC has demonstrated correlation with central venous pressure and right atrial pressure (as a proxy for left atrial pressure) as it flows directly into the right atrium (and by extension left atrial pressure through the connection through the pulmonary circulation), and it may correlate with renal function and renal sodium retention, which are also very important prognostic factors of heart failure. Therefore, increasing IVC volume and/or pressure may be a very effective early indicator of worsening heart condition.

In addition to heart failure patients, hemodialysis patients have a chronic need for careful volume management. Since their kidneys aren't excreting fluid, they are constantly becoming overloaded with fluid. Furthermore, large volumes of fluid are involved in the hemodialysis process, and managing patients so that they don't end up hypovolemic or overloaded with fluid requires careful management.

There are other groups of patients who might benefit from such a monitor. For example, patients in septic shock or acute shock due to trauma are subject to hypoperfusion.

Current Approaches to Monitoring the IVC or Other Blood Vessels

Prior studies of IVC dimensions have been conducted using external ultrasound imaging. This typically requires a highly trained physician or ultrasound technician to manage the ultrasound machine, ensure an appropriate connection of the transducer to the skin, position the ultrasound transducer in the appropriate location, identify the IVC, and take accurate measurements. This is not something that heart failure patients or their caregivers could typically be trained to do predictably and accurately with existing equipment. Moreover, these systems typically include large, complex, and expensive pieces of equipment which are not suitable for use outside of a specialized medical facility and are therefore not designed for serial measurements for chronic monitoring purposes.

Recent studies have indicated that the variation in IVC diameter over the respiratory cycle may be a more sensitive measurement of fluid overload and/or heart failure than simple measurement of average IVC diameter, volume, or pressure. During inspiration, intrathoracic pressure decreases, thereby increasing venous return and causing collapse of the IVC. During expiration, intrathoracic pressure increases, decreasing venous return and causing an increase in the diameter of the IVC.

While vessel dimensions may be measurable using external ultrasound, magnetic resonance imaging, computerized axial tomography, or other technologies, these imaging procedures must be administered in a hospital or other specialized facility. Furthermore, such procedures do not permit continuous monitoring, and do not allow for monitoring of the patient at their home or other remote location. As a result, the condition of a heart failure patient can worsen into a critical state before care providers become aware of it, dramatically increasing the mortality risk and cost of treatment for the patient.

PCT publication numbers WO2016/131020 and WO2017/024051, assigned to the assignee of the present disclosure, describe approaches involving implanted and catheter-based devices for real time monitoring of IVC dimensions for the diagnosis and treatment of heart failure and other conditions.

The present disclosure is directed towards providing improved apparatus for blood vessel dimension monitoring.

SUMMARY OF THE DISCLOSURE

According to the present invention there is provided an implantable ultrasonic vascular sensor for implantation at a fixed location within a vessel, comprising:
  at least one ultrasound transducer;
  a transducer drive circuit; and
  means for wirelessly transmitting ultrasound data from the at least one ultrasound transducer.

The at least one ultrasound transducer may comprise a first transducer for transmitting an ultrasound wave and a second transducer for receiving an ultrasound echo.

The implantable ultrasonic vascular sensor may be configured for untethered retention in a vessel. In other words, there is no catheter attached to the implant after implantation. By "implantation at a fixed location" it is meant that the sensor is an implant, not a catheter.

The implantable ultrasonic vascular sensor is intended for retention in a vessel following withdrawal of a deployment catheter.

The at least one ultrasound transducer may comprise means for supporting the first transducer and the second transducer opposite one another.

The at least one ultrasound transducer may comprise means for supporting the first transducer and the second transducer adjacent each other.

The implantable ultrasonic vascular sensor may comprise means for supporting the first transducer and the second transducer back to back.

The implantable ultrasonic vascular sensor may further comprise a passive reflector attachable to a vessel wall.

The implantable ultrasonic vascular sensor may comprise a plurality of pairs of first and second transducers.

The implantable ultrasonic vascular sensor may further comprise means for supporting the plurality of pairs of first and second transducers for measuring across different chords of a vessel.

The or each transducer may be configured to transmit an ultrasound wave and receive an ultrasound echo.

The at least one transducer may be configured to provide an ultrasound wave having a beam width of between 5° and 14°.

The implantable ultrasonic vascular sensor may be configured to operate in real time for real time vessel monitoring.

The transducer drive circuit and at least one transducer may be configured to operate at a frequency in the range of 4 MHz to 20 MHz.

The transducer drive circuit and at least one transducer may be configured to operate at a frequency in the range of 7 MHz to 15 MHz.

The implantable ultrasonic vascular sensor may comprise a plurality of transducers. The drive circuit may configured to time multiplex operation of the transducers.

The implantable ultrasonic vascular sensor may further comprise a support structure for supporting the or each transducer within a vessel.

The support structure may have a stent-like configuration for engaging a vessel wall around its periphery.

At least one transducer may be longitudinally separated from a main portion of the support structure.

At least one transducer may be mounted on a strut extending longitudinally from the support structure main portion.

The strut may be mechanically biased to lie against a vessel wall.

Preferably the support structure has little impact on physiological expansion or contraction of the vessel at a sensing site. In other words, in use, the support structure and the transducer(s) move with the vessel wall. A movement of the vessel wall in a radial direction would impart a corresponding movement of the transducer(s) in a radial direction.

The strut may comprise an anchor for direct anchoring to a vessel wall.

The anchor may extend from a tip of the strut.

The strut may comprise a coating to promote adhesion to a vessel wall.

The at least one transducer may include a piezoelectric element and associated electrodes.

The at least one transducer may comprise a matching layer on an ultrasonic signal path side of the piezoelectric element and having a thickness of approximately a quarter of the wavelength of operation of the piezoelectric element.

The at least one transducer may comprise an active piezoelectric layer with a thickness of approximately a half wavelength.

The at least one transducer may have a backing material for attenuation of emitted ultrasonic waves in a direction opposed to a preferred signal direction.

The backing material may comprise a carrier material with embedded particles.

The at least one ultrasound transducer may comprise:
- a piezoelectric layer and first and second opposed electrodes on said piezoelectric layer;
- a backing material configured to attenuate ultrasound waves and minimize reflection thereof in a direction away from a vessel volume; and
- a matching layer having acoustic properties for optimizing ultrasound waves between said matching layer and blood in contact therewith;
- wherein the transducer is configured to be positioned along a wall of the vessel with the matching layer exposed to blood and facing an opposing wall of the vessel.

The implantable ultrasonic vascular sensor may further comprise means for measuring an acoustic wave time of flight between an ultrasound transmitter and an ultrasound receiver.

The implantable ultrasonic vascular sensor may further comprise means for calculating the distance between the ultrasound transmitter and the ultrasound receiver based on the measured time of flight.

In accordance with the present invention there is further provided a blood vessel monitoring system comprising at least one implantable ultrasonic vascular sensor as described above, and a remote processor configured to receive the transmitted ultrasound data and calculate distance between the ultrasound transmitter and the ultrasound receiver based on the measured time of flight.

The blood vessel monitoring system may further comprise means for determining at least one blood vessel dimension from the received data.

The blood vessel monitoring system may further comprise means for recognizing a plurality of diffuse ultrasound echo wave responses and means for determining a value representing vessel diameter or diameter changes from said responses.

The blood vessel monitoring system may further comprise means for determining at least one parameter value derived from a blood vessel dimension.

The implantable ultrasonic vascular sensor may comprise a plurality of transducers arranged to transmit and receive across different chords, and the signal processing circuit may be configured to use data from said transducers to determine blood volume and/or vessel shape.

The signal processing circuit may be configured to operate according to a desired user pattern such as intermittent or continuous or a hybrid of intermittent and continuous.

The blood vessel monitoring system may comprise a component configured to be mounted internally in the patient and an external component outside the patient's body, and said components are configured to wirelessly communicate.

The blood vessel monitoring system may comprise a subcutaneous component arranged to communicate with the implantable ultrasonic vascular sensor provide the communication link to an external component.

The blood vessel monitoring system may further comprise a discrete power source arranged to be implanted subcutaneously at a remote location separated from the vascular implant.

The blood vessel monitoring system may further comprise a discrete power source arranged to be implanted subcutaneously at a location separated from the implantable ultrasonic vascular sensor.

In accordance with the present invention there is further provided a vascular monitoring method comprising:
- implanting at least one ultrasound transducer within a vessel;
- providing a drive signal to the at least one ultrasound transducer;
- generating and transmitting an ultrasound wave;
- detecting an ultrasound echo;
- recording a time delay between the transmission of the ultrasound pulse and the detection of the ultrasound echo; and
- wirelessly transmitting ultrasound data from the at least one ultrasound transducer.

Implanting at least one ultrasound transducer within a vessel may comprise implanting at least one ultrasound transducer within an inferior vena cava, IVC.

The ultrasound wave may have a beam width of between 5° and 14°.

The at least one transducer may be operating at a frequency in the range of 4 MHz to 20 MHz.

The at least one transducer may be operating at a frequency in the range of 7 MHz to 15 MHz.

The method may further comprise calculating the distance between an ultrasound transmitter and an ultrasound receiver based on the time delay and wirelessly transmitting the distance.

The method may further comprise receiving the transmitted ultrasound data at a remote processor and calculating the distance between the ultrasound transmitter and the ultrasound receiver based on the time delay.

The method may further comprise determining at least one blood vessel dimension from the received data.

The method may further comprise recognizing a plurality of diffuse ultrasound echo wave responses and determining a value representing vessel diameter or diameter changes from said responses.

The method may further comprise determining at least one parameter value derived from a blood vessel dimension.

The method may further comprise using data from multiple transducers to determine blood volume and/or vessel shape.

The method may further comprise operating according to a desired user pattern such as intermittent or continuous or a hybrid of intermittent and continuous.

We describe a system for monitoring a blood vessel, the system comprising:
- an implantable support structure configured to engage a blood vessel wall,
- an ultrasonic sensor including one or more transducers mounted on or to the support structure at an orientation to direct ultrasonic waves across the vessel, and to receive ultrasonic waves,
- a drive circuit for driving the transducer, and
- a signal processing circuit for processing sensor outputs to monitor vessel width dimension and/or changes in dimension.

Preferably, the support structure has a stent-like configuration for engaging a vessel wall around its periphery.

Preferably, at least one transducer is longitudinally separated from a main portion of the support structure, so that the structure main portion is substantially not in the path of ultrasonic waves and has little impact on physiologic expansion or contraction of the vessel at a sensing site.

Preferably, at least one transducer is mounted on a strut extending longitudinally from the support structure main portion.

In one example, the strut comprises an anchor for direct anchoring to a vessel wall in addition to being supported by the support structure. In one embodiment, the anchor extends from a tip of the strut.

In one example, the strut comprises a coating to promote adhesion to a vessel wall.

In some embodiments, the system comprises a passive reflector having an ultrasonic mismatch from blood, and being attachable to a vessel wall.

Preferably, the system comprises separate transducers for transmitting and receiving, in which at least one pair of transmit and receive transducers are arranged on the implant to be on opposite sides of the vessel. The system may comprise transmit and receive transducers which are separate or integrated, in which at least one transducer or transducer pair is arranged at approximately the same radial position in order to transmit an ultrasonic wave and receive a corresponding echo. In one embodiment, the sensor comprises a plurality of physically separate transducers mounted on a longitudinal strut extending from the support structure.

Preferably, the sensor comprises a plurality of pairs of transmit and receive transducers, arranged for measuring across different chords such as relatively orthogonal diameters of a vessel.

Preferably, at least one transducer includes a piezoelectric element and associated electrodes.

In one example, at least one transducer comprises a matching layer on an ultrasonic signal path side of the piezoelectric element and having a thickness of approximately a quarter of the wavelength of operation of the piezoelectric element.

Preferably, at least one transducer has an active piezoelectric layer with a thickness of approximately a half wavelength.

In one embodiment, at least one transducer has a backing material for attenuation of emitted ultrasonic waves in a direction opposed to a preferred signal direction.

Preferably, the backing material comprises a carrier material with embedded particles so that a wave emanating from the vibrating piezoelectric layer back surface in an unintended direction, such as away from a target and into the backing material, is absorbed and does not reflect back into a blood vessel in use.

In one example, at least one transducer comprises:
- a piezoelectric layer and first and second opposed electrodes on said piezoelectric layer,
- a backing material configured to attenuate ultrasound waves and minimize reflection thereof in a direction away from a vessel volume; and
- a matching layer having acoustic properties for optimizing ultrasound waves between said matching layer and blood in contact therewith;
- wherein the transducer is configured to be located along a wall of the vessel with the matching layer exposed to blood and facing an opposing wall of the vessel.

Preferably, the transducer provides an ultrasound wave having a beam width of between 5° and 14°.

Preferably, the sensor and the circuit are configured to operate in real time for real time vessel monitoring.

In one example, the circuits comprise a component configured to be mounted internally in the patient and an external component outside the patient's body, and said components are configured to wirelessly communicate.

Preferably, the system comprises a subcutaneous component arranged to communicate with the sensor and provide the communication link to an external component.

Preferably, the system comprises a discrete power source arranged to be implanted subcutaneously at a location separated from the vascular implant.

Preferably, the drive circuit and at least one transducer are configured to operate at a frequency in the range of 4 MHz to 20 MHz, and preferably at least 7 MHz.

In one example, the drive circuit and at least one transducer are configured to operate at a frequency in the range of 7 MHz to 15 MHz.

Preferably, the sensor comprises a plurality of transducers and the drive circuit is configured to time multiplex operation of the transducers.

Preferably, the signal processing circuit is configured to recognize a plurality of diffuse ultrasound echo wave responses and to determine a value representing vessel diameter or diameter changes from said responses.

Preferably, the signal processing circuit is configured such that received waveform undergoes a Hilbert transform, whereby the timers stop when an echo waveform envelope exceeds a certain level.

In one example, the signal processing circuit is configured to determine at least one parameter value derived from a blood vessel dimension, such as blood volume.

Preferably, the sensor comprises a plurality of transducers arranged to transmit and receive across different chords, and the signal processing circuit is configured to use data from said transducers to determine blood volume and/or vessel shape.

Preferably, the signal processing circuit is configured to operate according to a desired user pattern such as intermittent or continuous or a hybrid of intermittent and continuous.

The disclosure also provides a non-transitory computer readable medium comprising software code for performing by a digital processor operations of a drive circuit and/or a signal processing circuit of a system of any embodiment.

BRIEF DESCRIPTION OF THE DRAWINGS

The disclosure will be more clearly understood from the following description of some embodiments thereof, given by way of example only with reference to the accompanying drawings in which.

DETAILED DESCRIPTION

In various embodiments, blood vessel monitoring systems are described which include an implant with a sensor having at least one ultrasonic transducer, a data processing subsystem, a communications subsystem, and a battery power source. The transducers are supported by a stent-like support structure for both anchoring and positioning the device within a vessel such as the IVC. The support structure is flexible, elastic and highly compliant, having little influence on the normal movement and shape of the IVC.

In this specification the term "transducer" is intended to mean an ultrasound device including actively vibrating material such as a piezoelectric material and also including associated parts such as a matching layer and a backing layer. A "sensor" is an assembly of one or more transducers and all components involved for ultrasound transmitting and receiving including in some embodiments a passive reflector, as described in more detail below. The specific transducing part in which an applied voltage is transformed into mechanical vibrations is referred to as the piezoelectric material or layer.

Figure 1:
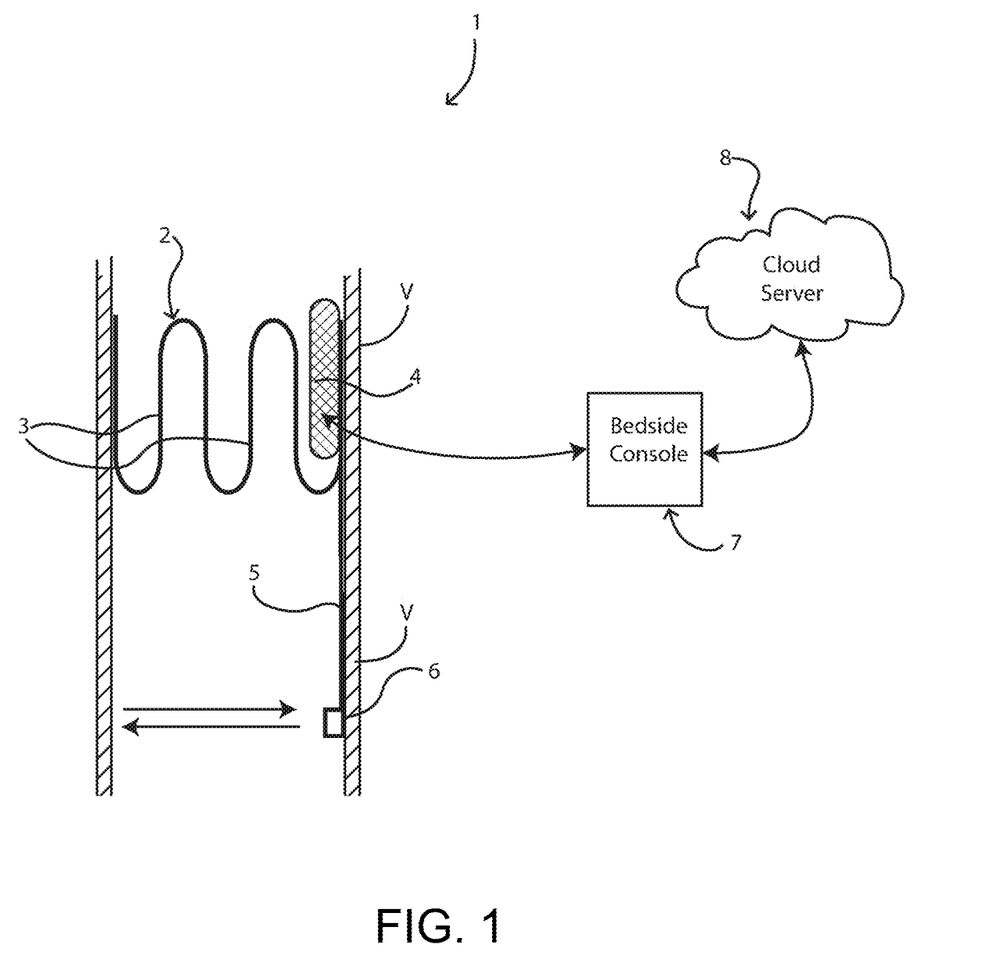
FIG. 1 is a diagram showing an intravascular ultrasound measurement system having an implantable device or "implant" and a bedside console for communication with the implant, data logging, data processing, and for upload of data to local and/or remote servers.

Referring to FIG. 1, a system 1 comprises an implant 2-6 with a stent-like support structure 2 with a wave pattern 3 forming a hoop, and supporting an electronics housing 4. A longitudinal strut 5 extends from the structure 2, and is mechanically biased to be against a vessel wall (V), in use. An ultrasound transducer 6, comprising a piezoelectric active layer, is mounted on the strut 5, so that it is longitudinally spaced-apart from the structure 2, thereby having an unimpeded path across to the opposite side of the blood vessel and being spatially separated from the structure 2 so that the vessel is measured at a point which is not at risk of being constrained or distorted by the structure 2. The longitudinal strut 5 is configured to maintain the transducer 6 against the vessel wall while allowing the transducer 6 to move radially inwardly and outwardly with the wall during vessel contraction and expansion respectively. The transducer 6 is supported to be against the wall, and hence the strut 5 could in various embodiments be bowed, straight, angled, wavy, spring-loaded or have any other configuration to bias the transducer 6 against the vessel wall.

The system 1 also comprises a bedside console 7 wirelessly linked with the electronics housing 4 of the implant via a wireless transmitter in electronics housing and also linked with cloud servers 8, or any other data collection and processing equipment.

Support Structure 2 and Transducer Strut 5

The support structure 2 is sufficiently flexible and elastic to have little influence on the normal movement and shape of a blood vessel such as the IVC while still remaining in a fixed location in the vessel. Additionally, the longitudinal separation of the transducer 6 from support structure 2 helps to isolate it from any distortion of the vessel caused by support structure 2.

The strut 5 has a Nitinol spine alongside which are insulated electrical leads for the transducer 6.

In some embodiments, the transducer 6 and/or longitudinal strut 5 may be configured to be fixed to the vessel wall to ensure that the transducer moves with it. For example, the transducer 6 and/or the longitudinal strut, and/or the support structure 2 may have barbs, hooks, or other features on its outer side that penetrate or engage the wall tissue. The transducer 6 and/or longitudinal strut 5 may alternatively or additionally be coated with a material that adheres to tissue or encourages tissue growth around or into these components. In other embodiments the longitudinal strut 5 may have a tip extending beyond the transducer 6 and configured to penetrate into the vessel wall.

The structure 2 diameter is preferably in the range of 5 mm to 40 mm, and the length is preferably in the range of 10 mm to 40 mm. In one example the transducer 6 has a width of 4 mm, a thickness of 3 mm, and a length of 3 mm, and the tubular electronics housing 4 with domed ends, has a diameter of 5 mm and a length of 10 mm.

The ultrasound transducer 6 is positioned such that it lies on the endothelium of the IVC wall, directing ultrasound pressure waves towards the diametrically opposing side of the IVC interior wall. Due to the acoustic impedance difference between the vessel wall and blood, the IVC wall is a significant reflector of ultrasound waves. Hence, the ultrasound waves are reflected from the opposing IVC wall, returning back to the ultrasound transducer where they are detected. The time delay between the transmitted ultrasound pulse and the received echo signal is recorded, allowing for the IVC diameter to be calculated.

In various embodiments, the support structure 2 may have one, two, or more rings or hoops and interconnecting longitudinal members or struts between the hoops, the hoops being resiliently biased radially outwardly in a stent-like manner to engage the vessel wall and securely anchor the device 2-6 in the vessel. The rings or hoops may have a sinusoidal, zig-zag, or other radially collapsible configuration to facilitate delivery through the vessel to the desired location of placement and to impart a relatively consistent radial fixation force against the vessel wall over a wide range of diameters.

Ultrasound Transducer

Figure 2:
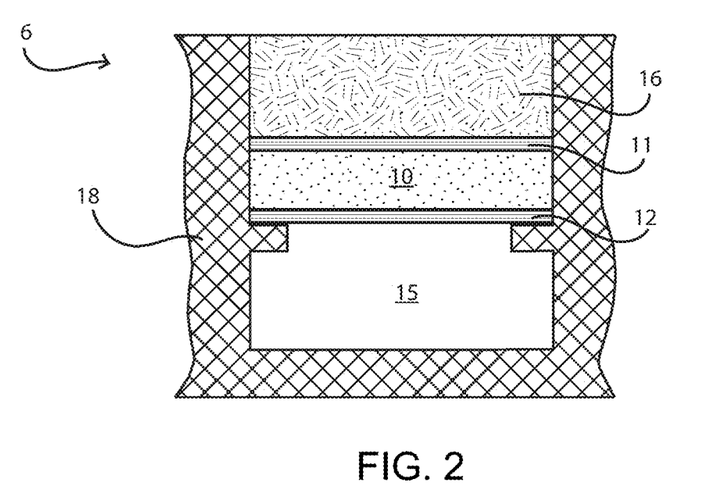
FIG. 2 is a cross-sectional view showing the multiple layers of an ultrasound transducer of the implant.

Referring to FIG. 2 the transducer 6 is shown diagrammatically in section. There is a piezoelectric layer 10 at its core, with electrodes 11 and 12 above and below, and a backing material 15 mounted between the active layer 10 and the transducer housing 18. There is also a matching layer 16 over the electrode 11. These layers are mounted within a sealed housing 18 of biocompatible polymeric material. The matching layer 16 is for direct contact with the blood in the vessel.

The piezoelectric material might be a piezoelectric ceramic, a piezoelectric single crystal or a piezoelectric composite material. The piezoelectric material may be diced in one direction or in orthogonal directions for reduction of lateral mode oscillations, due to lateral dimensions which approach a full wavelength.

In one embodiment, the piezoelectric layer is suitable to be driven at 4 MHz and has a thickness of 1.0 mm, and the other layers of the transducer raise this to a total thickness value in the range of 4 to 6 mm. In various embodiments the piezoelectric material might need to be in excess of 3 mm in width, and might preferably be made in a composite to break up lateral modes.

Up to limits, higher drive frequencies are preferred because a sharper beam is created, increasing signal strength and decreasing the possibility of echoes from parts of the vessel other than the diametrically opposed side. Higher frequencies have their limit, however. Blood attenuation is approximately 0.15 dB/MHz/cm. So, for a 2 cm diameter vessel, at 5 MHz, the attenuation is 3 dB, while at 20 MHz it is 12 dB. In the 30 MHz range, echoes from blood begin to compete in amplitude from those of tissue, and wall determination becomes yet more difficult. Therefore the preferred range of drive frequency is 4 MHz to 20 MHz, and more preferably 7 MHz to 15 MHz.

In general, the piezoelectric material thickness scales inversely proportionately to the frequency of operation.

The transducer may have a single piezoelectric crystal, or a composite "pillar" structure. The pillar transducer construction may provide a lower noise signal with better signal to noise ratio, and a relatively small aperture. A single crystal piezoelectric layer would have better amplitude conversion (voltage to displacement, and reverse) but would draw a higher current.

The matching layer 16 preferably has a thickness of a quarter wavelength.

The overall transducer may be mounted with an air gap or backing material 15 on the back side. This feature is to ensure that the waves emanating from the vibrating piezoelectric material in the unintended direction (i.e. away from the target and into the backing material), is absorbed and does not reflect back into the piezoelectric material. As shown in FIG. 2, in this embodiment there is backing material 15 of an epoxy with cork particles, chosen to have a thickness for good attenuation.

The ultrasound transducer beam profile is mainly dependent on excitation pulse frequency. For example, 4 MHz with a 3 mm aperture gives a 6 dB beam width of 24°, 8 MHz gives 12°, and 10 MHz gives 9°. When targeting non planar surfaces, this can significantly affect sensor operation. There is a trade-off between beam width and angle-to-target and signal-to-noise ratio, with narrower beams providing higher signal-to-noise ratio.

Figure 3:
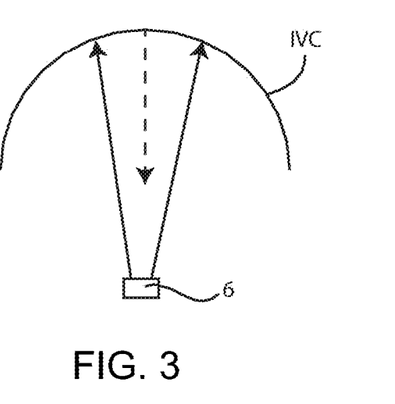
FIGS. 3 and 4 are sketches showing modes of operation of a transducer.
Figure 4:
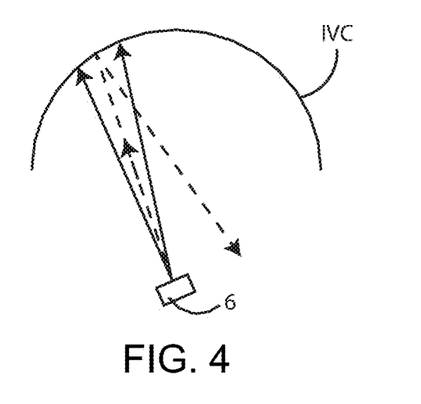

FIG. 3 shows a narrow beam of 10 MHz giving a 9° beam width normal to target, and therefore a good signal response. However, as shown in FIG. 4, a beam with these parameters results in the echo being missed in some circumstances. The transducer is preferably oriented such that the transmit signal is perpendicular to the opposing vessel wall to ensure that a maximum reflected signal is received by the transducer. However, perfect orientation may be challenging, and with vessel distension/contraction and other motion the angle of the vessel wall may change relative to the transducer. For this reason, a wider beam width may be more important to ensure a signal is received by the transducer.

Alternatively, as described in more detail below it may be preferred to rely on the echo structure from within the vessel wall to make measurements, as the strong specular reflection of the blood/wall interface may not always be achievable as compared to the diffuse echoes from within the vessel wall.

The following are exemplary aspects of the ultrasonic transducer for advantageous use in the application of monitoring width dimension of a blood vessel such as the IVC.

The matching layer 16 is preferably $\frac{1}{4}\lambda$ thick

The electrodes 11 and 12 are of gold or nickel, applied with In:Ag solder The backing material 15 is lamination epoxy, Epotek 301

The piezoelectric layer has a thickness of $\frac{1}{2}\lambda$, and an impedance of $Z_c \sim 33$ M Rayles The backing material has a thickness and a composition to be attenuative enough to prevent reflection with an impedance to shape waveform. This may alternatively be of a rubber material, preferably embedded with particles.

It is sub optimal if the width-to-thickness ratio of the transducer is in the range of $0.7 < W/T < 5.0$ Matching layer material 16 may be Henkle Loctite Stycast 3103 epoxy, $Z_m \sim 4.6$ M Rayls.

By way of example, for operation at 7.5 MHz, a CTS 3202HD piezoelectric ceramic with a thickness of approximately 0.3 mm (half wavelength) a surface dimension of 2.5 mm square, facing into the vessel was used. The ceramic was plated on both sides with approximately 0.2 microns of gold. The front surface matching layer material was a Henkel Loctite Stycast 3103 filled epoxy with an acoustic impedance of 4.6 MRayls, which was cast, adhesively bonded to the ceramic using EpoTek 301 epoxy, and lapped to one quarter wavelength thickness, as determined by impedance measurements. The backing material was alternatively air or a silicone rubber loaded with cork powder (acoustic impedance approximately 1.7 MRayls). 0.05 mm diameter copper leads were soldered to the opposing electrodes on the ceramic with 97:3::In:Ag solder. At approximately 30 mm from the ceramic, the leads were attached to either twisted pair wires or 50 Ohm coaxial cable for connection to the electronics.

Alternative Transducer Mounting Arrangements

Figure 5:
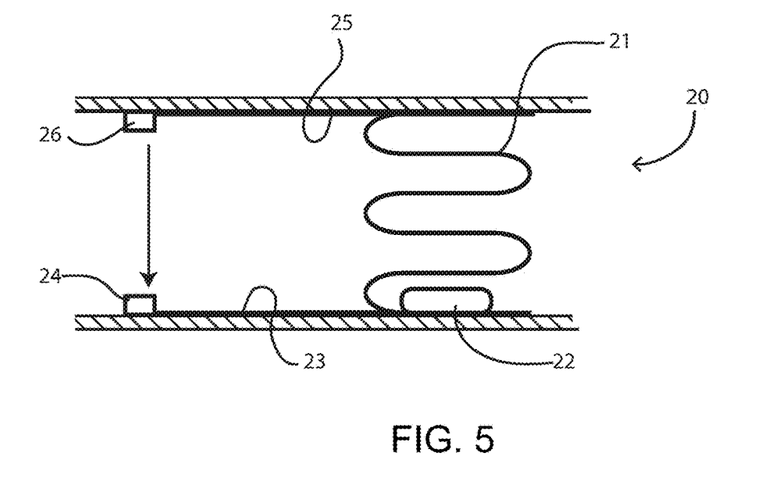
FIG. 5 is a diagram showing an implant having dedicated transmit and receive ultrasonic transducers mounted on diametrically opposed struts.

FIG. 5 shows an implant 20 with a support structure 21, electronics housing 22, two longitudinal struts 25 and 23 on which are transmit and receive transducers 26 and 24, respectively. In this arrangement, the acoustic wave time of flight between transmitter and receiver is only half of that for a single combined transmitter/receiver for which the ultrasound waves traverse a round trip. Further, the signal to noise ratio is better since there is no reliance on a weak echo from a tissue/blood interface. Signal processing is required to compensate for the thickness of both the transmitter and the receiver, and it is necessary to ensure that both struts 25 and 23 keep the respective transducer parts against the vessel wall. If the transmit and receive functions are separate, at opposite sides of a vessel such as in FIG. 5, the system processors do not need to take account of the quality of reflection from the vessel wall.

A major advantage of using separate transducers for transmit and receive functions is to isolate transmit ring-down noise from the received signal. This noise would make it extremely difficult to set a meaningful threshold. Note in particular the noise on the waveforms of FIGS. 10(a)-(d), immediately to the right of the transmit burst. With transmit ring-down noise, the time system would have to electronically clamp the signal to zero after transmission, and then open up sufficiently before wall echoes are anticipated.

Figure 6:
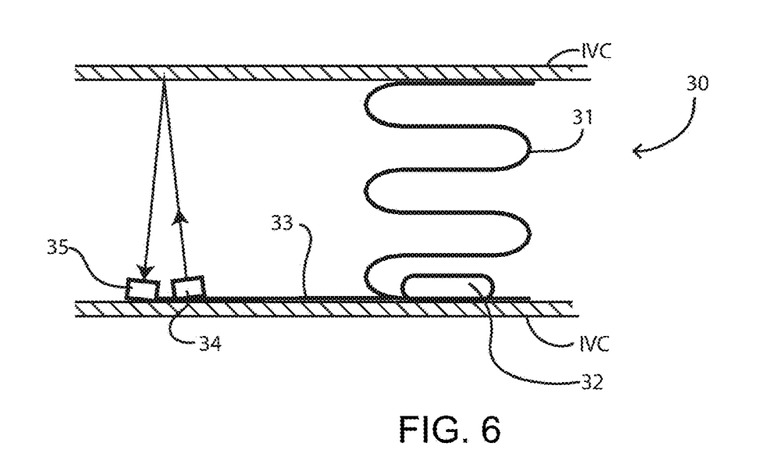
FIG. 6 is a diagram showing separate transmit and receive transducers mounted side-by-side on a single strut.

FIG. 6 shows an implant 30 with a support structure 31, electronic housing 32, a strut 33, and separate transmit and receive transducers 34 and 35 mounted adjacent to each other or linearly spaced apart on the same strut 33 on one side of the vessel. This arrangement allows a greater signal to noise ratio for signal processing with the avoidance of interference in the received echo signal from the transmit burst. Where the transmit and receive functions are separate and on the same strut, (FIG. 6) it is preferable that they are about 0.5 mm to 5 mm apart.

A system with two transducers deployed at a longitudinal distance from each other, either supported by the same or different support structures, may also be implemented to measure a Doppler shift in the received signal. This would allow an estimate of volume flow.

Figure 7:
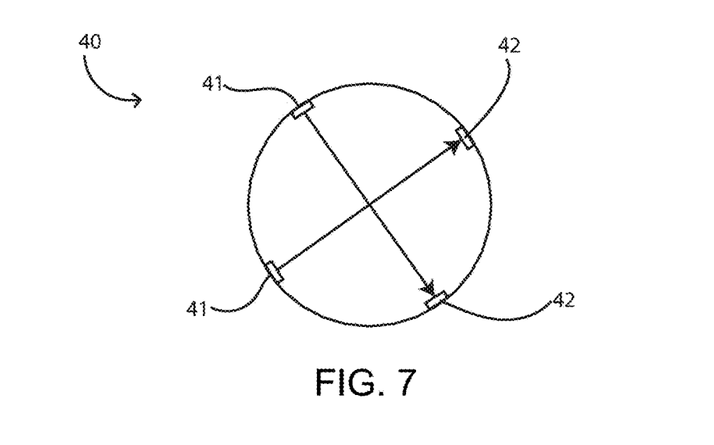
FIG. 7 shows an implant arrangement having two pairs of opposed transducers.

FIG. 7 shows a further configuration 40 having two pairs of transmit/receive transducers 41, 42 oriented at 90° relative to each other. This allows determination of diameters in two orthogonal directions. Advantageously this configuration allows both the anterior-posterior dimension and medial-lateral dimension to be monitored, allowing the processor to determine IVC geometry and blood volume. Also, it allows a digital processor to perform modelling of the vessel cross-section, for example to monitor major and minor axes. Such axes may be used to model the vessel cross-section as a parallelogram and possible ellipse. The circuits may be configured to perform data correction with parallelogram edge and diagonal correction, by averaging opposed parallelogram sides. Also, the circuits may be configured to perform ellipse reconstruction to model a vessel shape, based on chordal lengths such as parallelogram side calculations, and they may be configured to apply a correction to compensate for change from a round to elliptical shape of the support structure in end view.

It is envisaged that there may be more than two transmitter/receiver transducer pairs, e.g. up to four or more pairs of transducers, and the above benefits therefore also apply, providing even further data concerning the full volume and shape of the vessel.

It is also possible to position two transducers back-to-back near the middle of the vessel lumen. Then one transducer could be used to measure the distance to one wall, and the other could be used to measure the distance to the opposite wall. The sum of those distances is the diameter of the vessel.

A passive reflector may be provided to provide a strong reflection. This may be embedded within or individually anchored to the vessel wall opposite the transmit/receive transducer. Alternatively, a passive reflector may be mounted on a longitudinal strut attached to the support structure to which the transducer is coupled. Any such passive reflector provides increased reflectivity as compared to a blood/tissue interface.

In other embodiments there may be a co-implanted passive reflector or a second receive transducer on or within the opposing wall of the vessel. This reflector would serve to ensure a strong, perpendicular reflected signal back to the transducer. This reflector would need to be mounted so as not to impact the motion of the wall but remain in contact with it. The reflector may be on a longitudinal strut extending from the opposite side of the support structure 2, 180° apart from and parallel to the strut supporting the transmitter and receiver components. Alternatively a passive reflector may be mounted to or implanted within the wall of the vessel opposite the location of transducer. The passive reflector will be composed of a material having an impedance mismatch with vessel wall tissue and/or blood, causing a strong reflection of the transmitted ultrasound signal back to the transducer. The passive reflector may comprise a staple, button, barb, or rivet configured to penetrate or fasten to the inner wall of the vessel. Alternatively the passive reflector may comprise an injectable substance such as a flowable material, pellets, or beads which can be injected into the wall tissue.

Transducer Drive and Signal Processing

Figure 8:
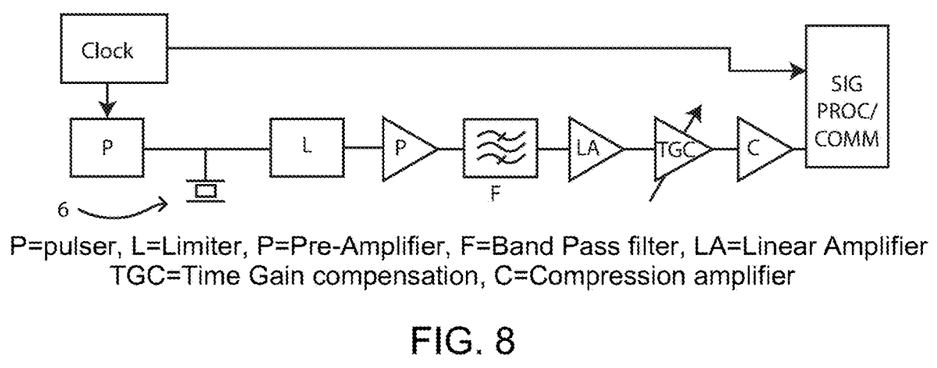
FIGS. 8 and 9 are circuit block diagrams for systems of two embodiments.

FIG. 8 shows a transducer drive circuit, in which there are components as follows: P (pulser), L (limiter), P (pre-amplifier), F (band-pass filter), LA (linear amplifier), TGC (time gain compensation), and C (compression amplifier). The transducer 6 is located immediately after the pulser P, the received signals being initially handled by the limiter L, followed by the pre-amplifier, band-pass filter, linear amplifier, time gain compensation, and the compression amplifier.

These components are within the implant electronics housing 4. The signal processor provides the wireless signals to the console 7 using Bluetooth, or an alternative local area wireless protocol. There may alternatively be a separate wireless communication interface or other wireless transceiver.

Figure 9:
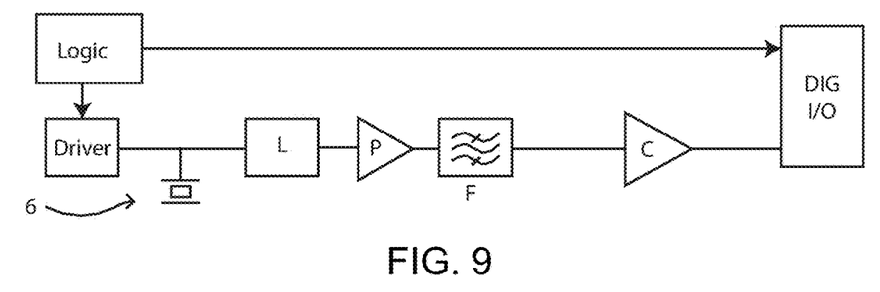
Figure 10A:
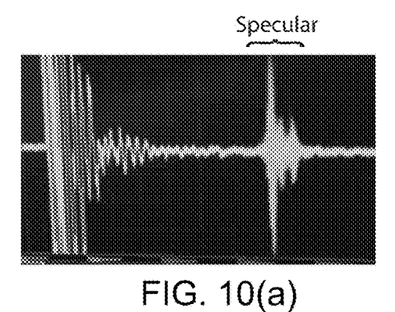
FIGS. 10(a) to 10(d) are plots showing ultrasound responses which are processed by a signal processor of a system of the disclosure.
Figure 10B:
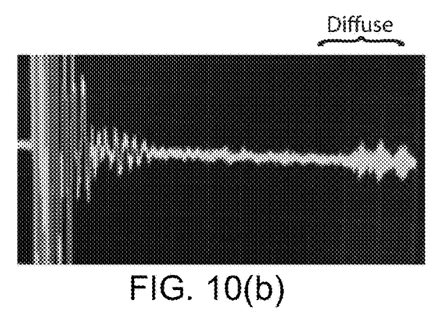
Figure 10C:
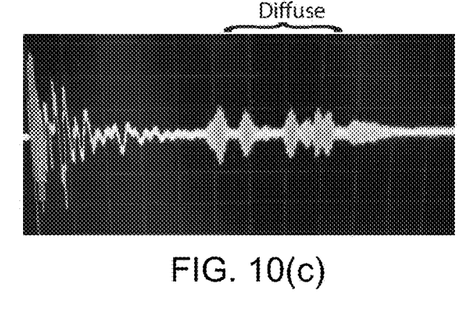
Figure 10D:
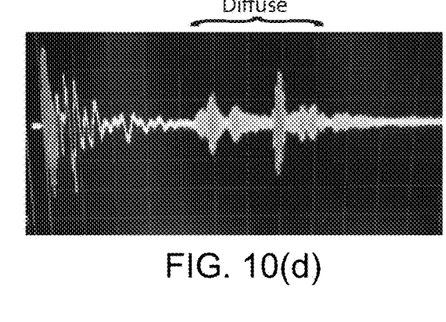

FIG. 9 shows a circuit which is suitable if integrated on a single chip, and the same annotation is used as in FIG. 8.

The component C is a compression amplifier, and a digital input/output function provides time of flight and other data to the external console.

Power is provided by an implantable battery source, of a type known in the art, which is encapsulated within the housing 4. Alternatively an extra vascular power source could be used, this could be located within a subcutaneous pocket, as per implanted pacemakers, and connected to the electronics unit via a lead.

The received ultrasound signals provide data which can be processed to give a complete and accurate measurement of the IVC dimensions and further, measurements of the blood flow, blood volume, blood pressure, and possibly blood chemistry including hematocrit and oxygenation. The ultrasound echo provides data representing a diameter of the blood vessel, and from this basic data a range of derived values may be calculated as noted above.

Signal processing may involve a full waveform analysis, preferably with averaging. It may include a comparator, implemented by a System on Chip ("SOC") or a microprocessor. The wiring may be twisted pairs or shielded coax. Alternatively, the signal processor may simply have a threshold signal intensity detector, which might require less electrical processing power.

Operation of the System and Data Analysis

The IVC contracts and expands with each respiration as well as with each cardiac cycle. Periodic IVC diameter measurements may thus be taken over multiple respiratory cycles, allowing for the recording of maximum and minimum diameters, from which a measure of collapsibility can be determined. The system may measure at any other desired intervals.

The recorded data is transmitted via radio frequency (RF) communication to the external console 6. In an alternative embodiment, some or all of the data may be locally stored on the implant. In general, the data processing, memory, and storage resources may be distributed in any suitable manner between the implant and the external equipment, provided the implant electronics unit is not excessively large, physically.

In another embodiment a subcutaneous monitor device may be provided to communicate with the implant, store the data, and to then transmit it to outside the body.

In one embodiment, the drive circuit sets a threshold, starts a timer on the transmit burst, and stops the timer on the first waveform crossing of the threshold. This number is then transmitted to the external processor. Alternatively, the received waveform undergoes a Hilbert transform, whereby the timers stop when the echo waveform envelope exceeds a certain level. This type of processing has significant advantages in signal-to-noise improvements.

Monitoring may be performed continuously or for intermittent periods, depending upon the desired trade-off between data intensity and battery life. It might be most efficient and physiologically relevant to take measurements only at night, when the patient is lying down and at rest. It might be desirable to intermittently measure IVC dimensions at random, or at specific time intervals. Although measurements may start and stop at random or preconfigured points along the respiratory cycle, it is intended that the measurement period cover multiple breathing cycles to enable IVC maxima and minima be identified.

Alternatively, the device may intermittently take continuous measurements over one or more entire cardiac and/or respiratory cycles, to get an effective measurement of the maximum and minimum IVC volumes. The difference between those minimum and maximum volumes may be an important prognostic indicator. If the overall IVC diameter is large and or there is only a small variation between minimum and maximum IVC diameters, that may be an indicator of congestion.

Referring to FIGS. 10(*a*)-(*d*), time moves from left to right, and it can be seen that a transmit pulse on the left is followed on the right by a number of receive echoes in some cases. Ideally one would like to see a strong well-defined received echo from the IVC wall, as seen in FIG. 10(*a*). However, we have found that most often ultrasound reflection from a vessel wall is in the form of multiple reflections, each from within the vessel wall. These layers are individual tissue mis-matches within the vessel wall.

A strong, well-defined received echo as in FIG. 10(*a*) results from a normal reflection off the vessel wall, and is not always achievable with the dynamic variations of the vessel. More commonly, a string of diffuse echoes as in FIGS. 10(*b*), 10(*c*), and 10(*d*) is achieved, wherein these weaker echoes result from the cellular structure of the vascular wall.

The signal processing of either the electronics on the implant, the bedside console, or the cloud server recognise such weaker sub-responses and may use for example edge detection (especially for diameter measurement) and/or averaging (especially for diameter variation tracking) to more accurately determine vessel diameter and/or collapsibility.

By way of background regarding diffuse reflection and specular reflection, IVUS images, and even echo cardiograms, rely on diffuse echoes, and where a normal reflection occurs (in cardiology, typically at the apex of the heart), a bright ring appears on the display. It would be preferable to have more specular reflections as shown in FIG. 10(*a*), but diffuse reflections, as shown in FIGS. 10(*b*) to (*d*), are more common.

Alternatives

There are embodiments where multiple, separate transducers are used as dedicated transmit and receive transducers in order to reduce noise in the system. These could also be used to measure the vessel in multiple planes, thus generating a more complex and accurate shape of the vessel rather than a simple single diameter. These transducers could also be longitudinally disposed along the length of the device to provide more predictable send receive response by limiting the curvature and angulation of the vessel at the target location.

The disclosure is not limited to the embodiments described but may be varied in construction and detail.

The invention claimed is:

1. An implantable ultrasonic vascular sensor configured to be implanted in a patient's inferior vena cava (IVC) at a fixed location within the IVC in contact with the IVC wall, comprising:
   at least one ultrasound transducer;
   a transducer drive circuit;
   an implantable support structure configured to move with physiological expansion and contraction of the IVC wall in response to changes in patient fluid volume, wherein said at least one transducer and transducer drive circuit are supported on the support structure, said at least one ultrasound transducer is supported to move with said expansion and contraction of the IVC wall when the support structure moves therewith; and
   means for wirelessly transmitting ultrasound data from the at least one ultrasound transducer.

2. The implantable ultrasonic vascular sensor of claim 1 wherein the at least one ultrasound transducer comprises a first transducer for transmitting an ultrasound wave and a second transducer for receiving an ultrasound echo.

3. The implantable ultrasonic vascular sensor of claim 2, comprising a plurality of pairs of first and second transducers.

4. The implantable ultrasonic vascular sensor of claim 3, further comprising means for supporting the plurality of pairs of first and second transducers for measuring across different chords of a vessel.

5. The implantable ultrasonic vascular sensor of claim 1, wherein the at least one transducer is configured to provide an ultrasound wave having a beam width of between 5° and 14°.

6. The implantable ultrasonic vascular sensor of claim 1, wherein the transducer drive circuit and at least one transducer are configured to operate at a frequency in the range of 4 MHz to 20 MHz.

7. The implantable ultrasonic vascular sensor of claim 1, wherein at least one transducer is mounted on a strut extending longitudinally from a support structure main portion.

8. The implantable ultrasonic vascular sensor of claim 7, wherein the strut is mechanically biased to lie against a vessel wall, wherein said at least one transducer is positioned to monitor a width dimension of the vessel by detecting the opposite vessel wall with a reflected ultrasound signal.

9. The implantable ultrasonic vascular sensor of claim 8, wherein the strut comprises an anchor for direct anchoring to a vessel wall.

10. The implantable ultrasonic vascular sensor of claim 1, wherein the at least one transducer comprises a matching layer on an ultrasonic signal path side of the piezoelectric element and having a thickness of approximately a quarter of the wavelength of operation of the piezoelectric element.

11. The implantable ultrasonic vascular sensor of claim 1, wherein the at least one transducer has a backing material for attenuation of emitted ultrasonic waves in a direction opposed to a preferred signal direction.

12. The implantable ultrasonic vascular sensor of claim 1, wherein the at least one ultrasound transducer comprises:
a piezoelectric layer and first and second opposed electrodes on said piezoelectric layer;
a backing material configured to attenuate ultrasound waves and minimize reflection thereof in a direction away from a vessel volume; and
a matching layer having acoustic properties for optimizing ultrasound waves between said matching layer and blood in contact therewith;
wherein the transducer is configured to be positioned along a wall of the vessel with the matching layer exposed to blood and facing an opposing wall of the vessel.

13. A vascular monitoring method, comprising:
implanting a support structure supporting at least one ultrasound transducer within a patient's IVC in contact with the IVC wall, wherein said support structure moves, expands and collapses with physiological expansion and contraction of the IVC wall in response to changes in patient fluid volume;
providing a drive signal to the at least one ultrasound transducer;
generating and transmitting an ultrasound wave;
detecting an ultrasound echo;
recording a time delay between the transmission of the ultrasound pulse and the detection of the ultrasound echo; and
wirelessly transmitting ultrasound data from the at least one ultrasound transducer.

14. The method of claim 13, wherein the ultrasound wave has a beam width of between 5° and 14°.

15. The method of claim 13, wherein the at least one transducer is operating at a frequency in the range of 4 MHz to 20 MHz.

16. The method of claim 13, further comprising receiving the transmitted ultrasound data at a remote processor and calculating with the processor the distance between the ultrasound transmitter and the ultrasound receiver based on the time delay.

17. The method of claim 16, further comprising recognizing a plurality a diffuse ultrasound echo wave responses and determining with the processor a value representing IVC diameter or diameter changes from said responses.

18. The method of claim 16, further comprising determining with the processor at least one IVC dimension from the received data, or at least one parameter value derived from an IVC dimension.

19. The method of claim 16, further comprising using data from multiple transducers to determine with the processor blood volume and/or IVC shape.

20. The implantable ultrasonic vascular sensor of claim 1, wherein:
at least one transducer is disposed on a portion of the support structure mechanically biased to lie against the IVC wall and move with said physiological expansion and contraction of the IVC wall; and
said at least one transducer is configured to monitor a change in width dimension of the vessel due to said physiological expansion and contraction in response to changes in patient fluid volume by detecting the opposite vessel wall with a reflected ultrasound signal.

21. An implantable ultrasonic vascular sensor configured to be implanted in a patient's inferior vena cava (IVC) at a fixed location within the IVC, comprising:
at least one ultrasound transducer;
a transducer drive circuit;
an implantable support structure configured to be implanted within the IVC in contact around a wall of the IVC and to move with physiological expansion and contraction of the IVC wall, wherein said at least one transducer and transducer drive circuit are supported on the support structure, said at least one ultrasound transducer supported to move with said physiological expansion and contraction of the IVC wall when the support structure moves therewith;
at least one passive reflector to reflect a signal from the at least one ultrasound transducer supported by said implantable support structure; and
means for wirelessly transmitting ultrasound data from the at least one ultrasound transducer.

* * * * *